United States Patent [19]

Delany

[11] Patent Number: 5,401,241
[45] Date of Patent: Mar. 28, 1995

[54] DUODENAL INTUBATION CATHETER

[75] Inventor: Harry M. Delany, Mount Vernon, N.Y.

[73] Assignee: Inamed Development Co., Carpinteria, Calif.

[21] Appl. No.: 879,804

[22] Filed: May 7, 1992

[51] Int. Cl.$^6$ .............................................. A61M 3/00
[52] U.S. Cl. ...................................... 604/43; 604/96; 604/102; 604/284; 604/280; 606/192
[58] Field of Search ................ 604/175, 102, 103, 45, 604/49, 54, 96, 270, 280, 43; 606/192, 194

[56] References Cited

U.S. PATENT DOCUMENTS

| | | | |
|---|---|---|---|
| 4,003,382 | 1/1977 | Dyke | 604/103 |
| 4,133,315 | 1/1979 | Berman et al. | 604/96 |
| 4,368,739 | 1/1983 | Nelson, Jr. | 604/54 |
| 4,485,805 | 12/1984 | Foster, Sr. | 604/96 |
| 4,543,089 | 9/1985 | Moss | 604/96 |
| 4,571,240 | 2/1986 | Samson et al. | 604/280 |
| 4,584,998 | 4/1986 | McGrail | 604/102 |
| 4,631,054 | 12/1986 | Kim | 604/280 |
| 4,642,092 | 2/1987 | Moss | 604/96 |
| 4,676,778 | 6/1987 | Nelson, Jr. | 604/45 |
| 4,704,111 | 11/1987 | Moss | 604/270 |
| 4,751,924 | 6/1988 | Hammerschmidt et al. | 604/103 |
| 4,899,747 | 2/1990 | Garren et al. | 604/103 |
| 4,944,745 | 7/1990 | Sogard et al. | 604/103 |
| 5,009,639 | 4/1991 | Kemling | 604/96 |
| 5,046,503 | 9/1991 | Schneiterman | 604/102 |
| 5,071,405 | 12/1991 | Piontek et al. | 604/284 |
| 5,098,378 | 3/1992 | Piontek et al. | 604/49 |
| 5,135,535 | 8/1992 | Kramer | 604/102 |
| 5,154,725 | 10/1992 | Leopold | 604/102 |

FOREIGN PATENT DOCUMENTS 8000007 1/1980 WIPO .

*Primary Examiner*—Randall L. Green
*Assistant Examiner*—Bob Clarke
*Attorney, Agent, or Firm*—Michael G. Petit

[57] ABSTRACT

An apparatus and method for the non-surgical direct intubation of the duodenum or small bowel. The apparatus consists of an introducer tube comprising a double-lumen tubular member having a proximal end and a distal end. One of the lumens is dimensioned to permit the passage of a duodenal catheter therethrough. The other lumen is in fluid communication with the interior of an inflatable, anatomically-conforming balloon affixed asymmetrically near the distal end of the introducer tube. The anatomically-conforming balloon is stomach shaped when inflated. The introducer tube is advanced through the esophagus until the balloon is within the confines of the stomach. The introducer tube is then rotated so that the balloon is oriented toward (inflates toward) the greater curvature of the stomach. As the balloon is inflated, it expands into and conforms with the interior shape of the stomach. Upon completion of the inflation, the distal end of the catheter lumen of the introducer tube is in juxtaposition with the pylorus. A duodenal catheter is inserted through the catheter lumen of the introducer tube into the duodenum. After placement of the duodenal catheter, the balloon on the introducer tube is deflated and the introducer tube removed, leaving the distal tip of the duodenal catheter within the duodenum.

3 Claims, 4 Drawing Sheets

DUODENAL INTUBATION CATHETER

BACKGROUND OF THE INVENTION

1. Field of the Invention

This invention relates to a novel nasogastric introducer tube and catheter for direct intubation of the duodenum or jejunum.

2. Prior Art

Failure of gastrointestinal functions may require intubation of the duodenum to facilitate feeding into and/or aspiration of the small bowel of the patient. Prior art intubation devices include both percutaneous endoscopically placed catheters and nasogastric tubes which may require endoscopic placement. An example of an endoscopically placed nasogastric tube is disclosed by Kim in U.S. Pat. No. 4,631,054. Kim's catheter comprises a flexible nasogastric tube with a mercury-filled bag circumferentially mounted near the distal tip of the catheter. The placement of Kim's catheter requires intubation with a gastroduodenoscope through which a flexible guidewire is introduced. The guidewire is advanced into the duodenum and the gastroduodenoscope removed. The catheter is then marked at the appropriate length and inserted through the nose over the guidewire and advanced to the mark. The guidewire is then removed leaving the distal tip of the catheter positioned within the duodenum. While Kim's method and catheter do not require fluoroscopic placement, it does require specialized endoscopic equipment for appropriate placement.

Nelson, Jr., in U.S. Pat. No. 4,368,739 discloses a long intestinal catheter for placement during open surgery. The catheter has a pair of inflatable balloons, the first one at its downstream end and the other a short distance upstream from the first one. The two balloons are inflated when the catheter approaches the duodenum to facilitate the manually directed passage into and through the duodenum. The catheter is then advanced through the duodenum and small intestine during surgery by manual manipulation of inflated balloons through an incision in the abdomen.

Moss, in U.S. Pat. Nos. 4,543,089 and 4,642,092, describes a gastric catheter which is used to aspirate gas and feed patients. The tube is placed percutaneously into the stomach by insertion of the tube through the abdominal wall by means of a laparoscopic trocar.

Notwithstanding the availability of the foregoing prior art devices, the success rate of getting nasogastric tubes through the pylorus and into the duodenum are as low as 50%. Fluoroscopic placement has improved the success rate of placement of duodenal tubes, but the process of passing a long tube into the duodenum through the pylorus still demands improvement especially for the seriously ill patient who cannot be conveniently or comfortably moved to radiology facility.

The use of prior art nasogastric tubes for feeding may result in aspiration pneumonia. This condition results when the integrity of the seal between the esophagus and the stomach is breached as, for example, by a stomach feeding tube passing therethrough. When an intubated patient is positioned laterally, the gastric contents may flow back along the tube up the esophagus where it may enter the trachea and be aspirated into the lung. This condition is particularly prevalent in the elderly. It is, therefore, desirable to provide a duodenal feeding tube which reduces the incidence of aspiration pneumonia and is easily placed without the need for surgery or fluoroscopic or endoscopic placement.

SUMMARY OF THE INVENTION

Tube feeding is generally regarded as a safe, efficient and relatively inexpensive method for feeding selected patients. Complications associated with the placement and use of feeding tubes have been described. Aside from the difficulty of successful placement, the major complication associated with prior art catheters is the relatively high incidence of aspiration pneumonia in elderly patients, that is, patients over 60 years old. This complication may be avoided by feeding into the duodenum instead of the stomach. It is therefore an object of this invention to provide a duodenal catheter assembly and method for the direct intubation of the duodenum and/or jejunum.

It is yet another object of this invention to provide an apparatus for the direct intubation of the duodenum without the necessity of specialized endoscopic equipment.

It is yet another object of this invention to provide a method and apparatus for the direct intubation of the duodenum which does not require the presence of radiological equipment.

It is another object of this invention to provide an apparatus and method for the direct intubation of the duodenum which has a high percentage of success when used by a practitioner of normal skill in the art. These and other objects of the invention will soon become apparent as we turn now to the drawings, which are illustrative of the invention.

DESCRIPTION OF THE PREFERRED EMBODIMENT

Figure 1:
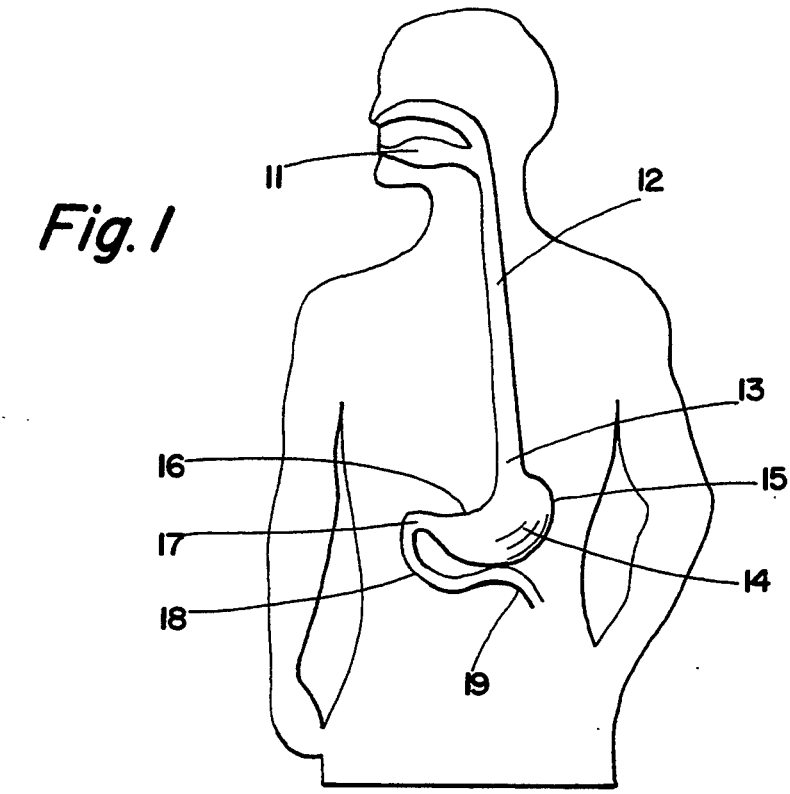
FIG. 1 is a schematic view of a portion of the gastrointestinal system of a human.

Turning now to FIG. 1, the upper digestive tract of the human is shown. The esophagus 12 terminates at the nose or mouth 11 at its superior end and at the stomach 14 at its inferior end. The esophageal-gastric juncture is denoted at 13. The wall of the stomach 14 encloses a chamber which is characterized, in part, by a first opening 13 to the esophagus (the gastro-esophageal juncture) and a second opening 17 (the pylorus) to the duodenum 18 and being generally a contoured sac having a greater curvature 15 and a lesser curvature 16. It is apparent from FIG. 1 that, when viewed from the front, the lesser curvature of the stomach hooks or curves to the left with respect to the esophagus. We will return to this point later. The stomach empties through the pylorus 17 into the duodenum 18. Gastric contents, after passing into the duodenum, continue on into the jejunum 19 and on into the ileum. For the reasons discussed above it is desirable to provide a means for inserting a tube through the nose or mouth, down the esophagus, through the stomach and pylorus and into the duodenum or jejunum without the need for specialized imaging or viewing equipment and with a high probability of success.

Figure 2A:
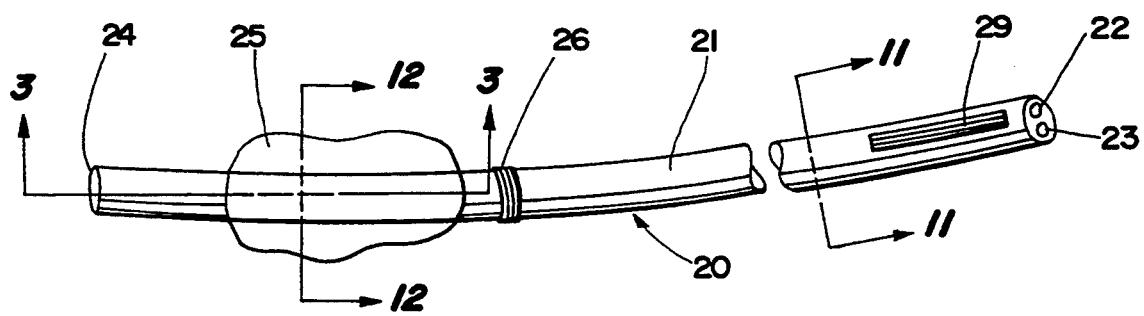
FIG. 2a is a perspective view of the distal portion of the novel duodenal catheter introducer tube of the present invention prior to inflation of the anatomically-conforming balloon.
Figure 2B:
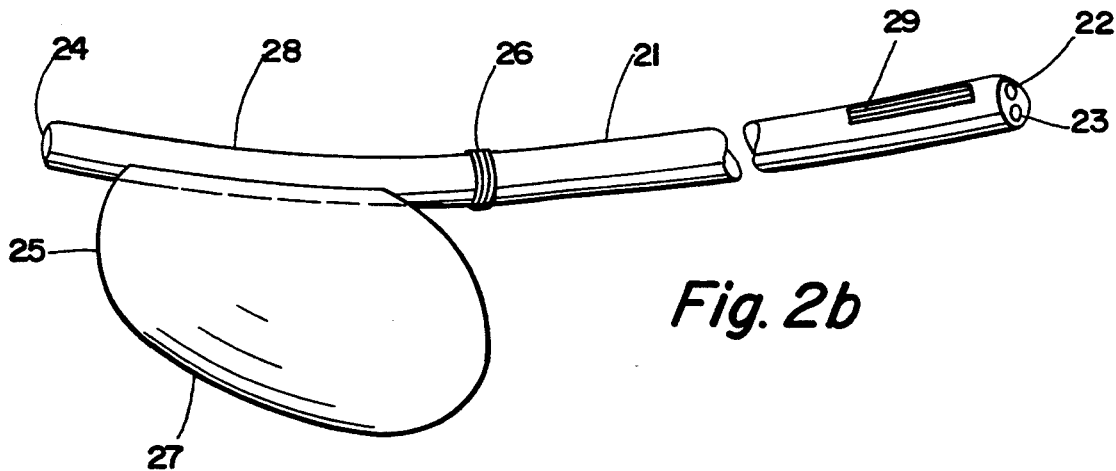
FIG. 2b is a perspective view of the duodenal catheter introducer tube of FIG. 2a with the anatomically-conforming balloon inflated.

The object of this invention is accomplished by means of an assembly comprising, in combination, a duodenal catheter, and a duodenal catheter insertion tube. Reference is now made to FIGS. 2a and 2b in which a duodenal catheter introducer tube, generally indicated at the numeral 20, has a proximal end and a distal end indicated at 24. Two conduits traverse the length of the introducer tube. The first conduit or lumen 22 is sufficiently large to accommodate the passage therethrough of a duodenal catheter of a type well known in the art. The second (parallel) conduit or lumen 23 is in fluid communication with the interior of an inflatable member 25 (alternatively referred to hereinafter as an "anatomically conforming balloon") which is affixed to the distal tip 24 of the intubation tube 20. The walls 21 of the intubation tube are generally smooth and elastomeric. A first marker 26 is affixed to the wall of the introducer tube proximal to the anatomically-conforming balloon 25 to enable a practitioner to determine by appropriate detection means when the marker and thus the balloon 25 is beyond the gastro-esophageal juncture 13 and entirely within the interior chamber of the stomach 14.

In practice, the practitioner inserts the distal tip 24 of the duodenal catheter introducer tube 20 into the nose and advances it through the esophagus and into the stomach. The position of the marker 26 is determined to verify the anatomically-conforming balloon 25 is entirely clear of the esophagus. A second marker 29 on the outer wall of the introducer tube remains visible when the first marker is within the stomach and indicates the orientation of the balloon within the stomach. The intubation tube 20 is rotated until the anatomically-conforming balloon 25 faces to the right so that it will inflate toward the greater curvature 15 of the stomach 14. The inflatable anatomically-conforming balloon 25 near the distal tip 24 of the introducer tube is then inflated by injecting an appropriate volume (~600 ml) of a fluid or air through the lumen 23. Once inflated, the balloon 25 conforms to the shape of the stomach as shown in FIG. 2b. The anatomically-conforming balloon portion 25 may be conveniently made by dipping a stomach-shaped mandril into a dispersion of silicone with repetitive curing. The resultant balloon may then be removed from the mandril and applied by means of a suitable adhesive to the distal tip of the introducer tube so that the introducer tube lies along the region of the balloon corresponding to the lesser curvature 16 of the stomach. Alternatively, the introducer tube may be attached to the mandril and dipped with the mandril so that the resulting stomach shaped inflatable member is vulcanized directly to the introducer tube.

Figure 3:
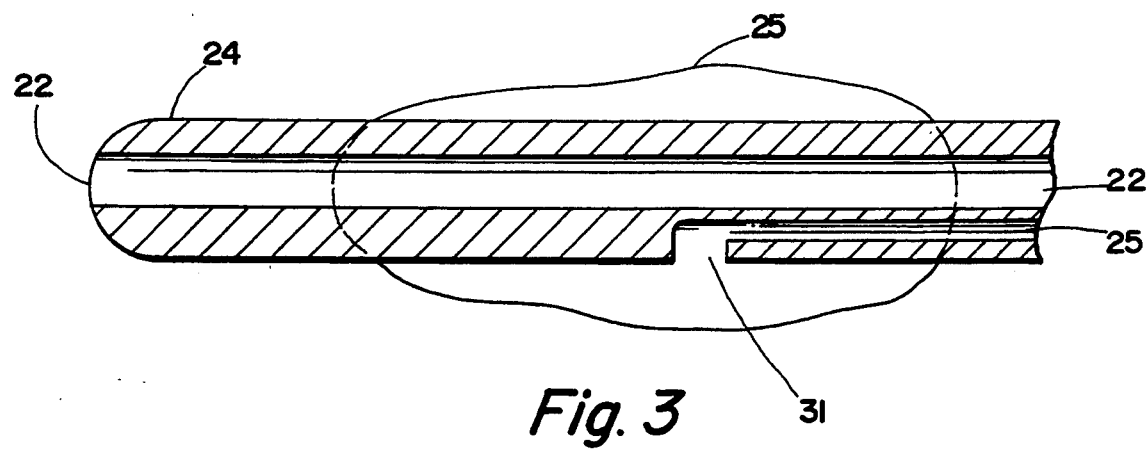
FIG. 3 is a cross-sectional view of the duodenal catheter introducer tube of FIG. 2a, along line 3—3.

The distal portion of the introducer tube is shown in greater detail now in FIG. 3. The distal portion has a central conduit 22 which emerges at the distal tip 24 of the introducer tube and which is dimensioned to accommodate the passage therethrough of a duodenal catheter. The distal tip 24 is smooth and contoured to facilitate passage through the esophagus 12 and gastro-esophageal orifice 13. The second lumen 23 is in fluid communication through a port 31 with the interior of the inflatable anatomically-conforming balloon member 25. Both lumen 22 and 23 extend substantially the entire length of the tube and have access ports on the proximal end of the introducer tube 20.

Figure 4:
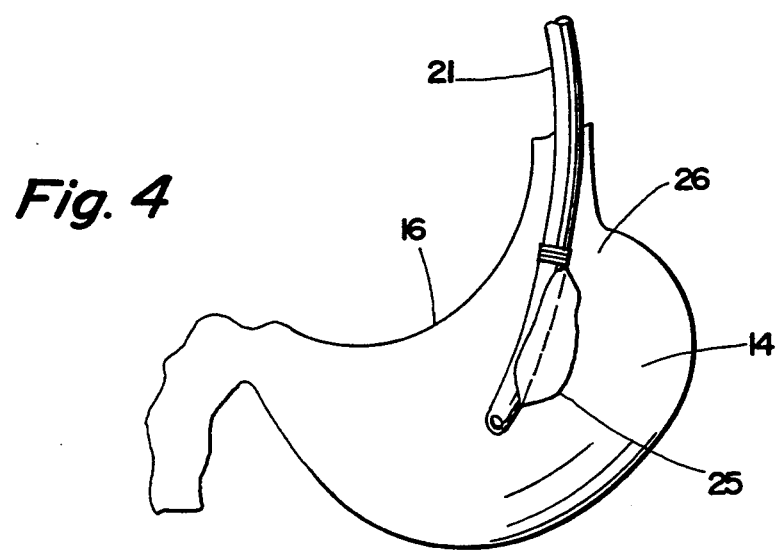
FIG. 4 is a schematic view of the distal tip of the duodenal catheter introducer tube of the present invention entering the stomach.
Figure 5:
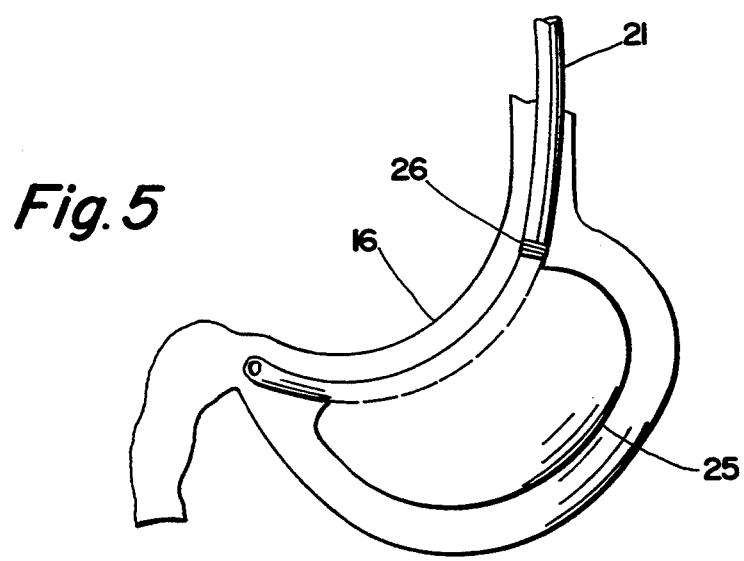
FIG. 5 is a schematic view of the distal portion of the duodenal catheter introducer tube of the present invention with the anatomically-conforming balloon inflated.

Reference now being made to FIGS. 4 through 8, the functioning of the introducer tube and the duodenal catheter may be best understood by turning first to FIG. 4. The introducer tube 20 is introduced through the nose into the stomach of a patient. It is important that the balloon portion be entirely within the stomach and beyond the gastro-esophageal juncture 13. This may be determined by the placement of a marker 26 such as a metallic element or even a magnet on the intubation tube proximal to and adjacent to the anatomically-conforming inflatable balloon 25. If the marker 26 comprises a metallic element, it may be conveniently detected by placing a metal detector on the chest below the esophagus and advancing the tube until the metal detector indicates that the marker 26 is beyond the gastro-esophageal juncture 13. Once it has been determined that the marker 26 is safely within the stomach, the introducer tube must then be rotated to orient the anatomically-conforming balloon 25 so that it is facing the greater curvature 15 of the stomach. The orientation of the balloon 25 is verified by observing the visual indicia 29 while rotating the intubation tube. The balloon should face to the right when viewed from in front of the patient. After positioning, the anatomically-conforming balloon 25 may be inflated as shown in FIG. 5. Approximately 600 ml of a fluid or air is injected through lumen 23 into the balloon 25 where it expands to take on the shape of the stomach interior. As the balloon's 25 shape conforms to the shape of the interior chamber of the stomach, the distal portion 28 of the introducer tube is forced against the lesser curvature 16 of the stomach 14 so that the distal tip 24 is in juxtaposition to the pylorus 18. Thus, the anatomically-conforming balloon 25 attached to the distal portion 28 of the introducer tube 20 serves to position the distal tip 24 of the introducer tube at the pylorus. Once the balloon 25 has been fully inflated and the distal tip 24 of the introducer tube 20 is in substantial juxtaposition with the pylorus 17, the duodenal catheter may be inserted.

Figure 6:
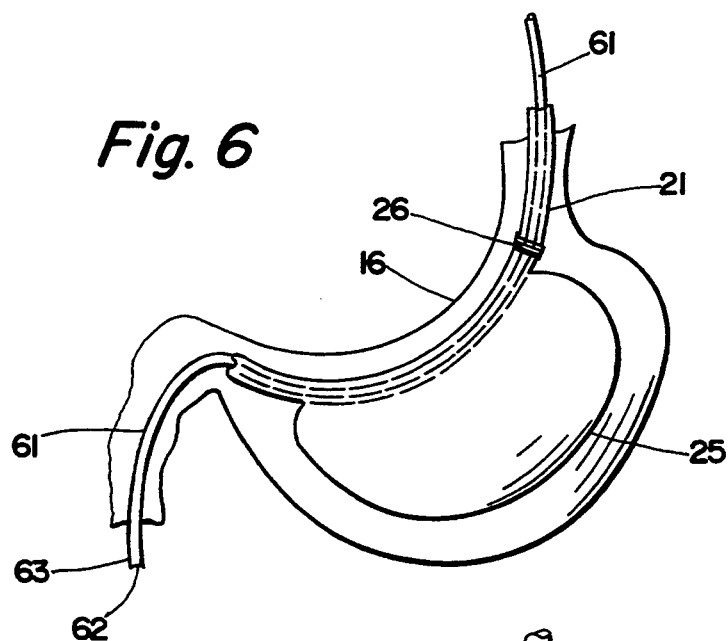
FIG. 6 shows the duodenal catheter advanced through the introducer channel in the duodenal catheter introducer tube, through the pylorus and into the duodenum.
Figure 7:
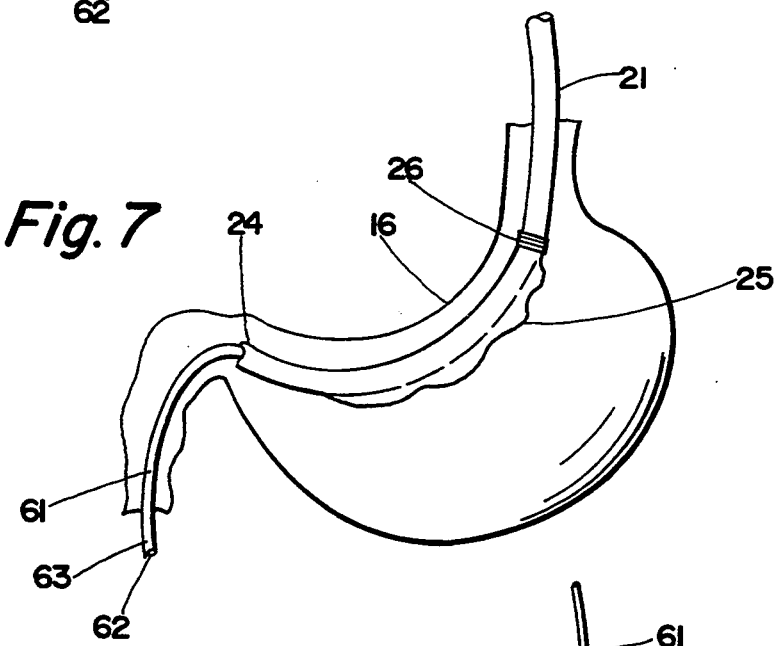
FIG. 7 is a schematic view of the distal tip of the duodenal catheter of the present invention positioned within the duodenum with the anatomically-conforming balloon on the duodenal catheter introducer tube deflated.
Figure 8:
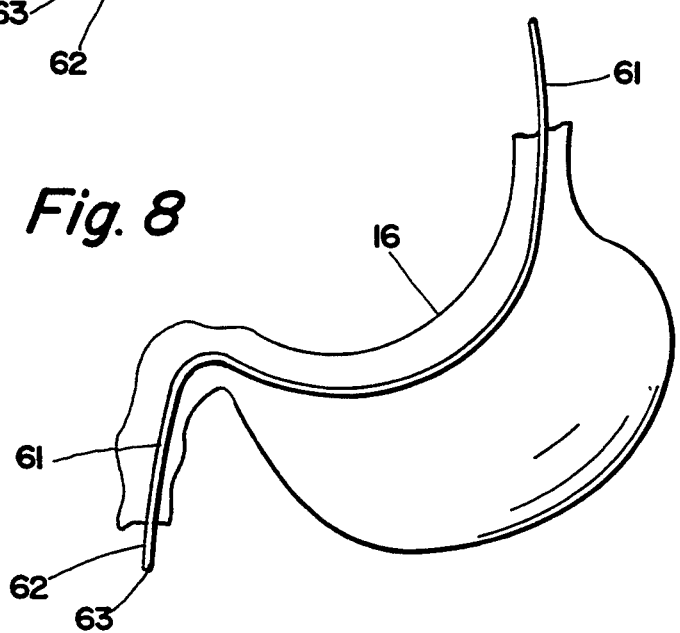
FIG. 8 is a schematic view of the duodenal catheter of the present invention with the distal tip positioned in the duodenum and the duodenal catheter introducer tube removed over the inner tube.

FIG. 6 shows the insertion of the duodenal catheter 61 through the central lumen 22 of the duodenal catheter introducer tube 20 and through the pylorus 17 into the duodenum 18. Once the tip 62 of the duodenal catheter 61 is through the pylorus 17 and reliably inside the duodenum 18, the anatomically-conforming balloon 25 on the introducer tube 20 may be deflated as shown in FIG. 7 and the introducer tube removed as shown in FIG. 8 leaving the duodenal catheter in place.

Figure 9:
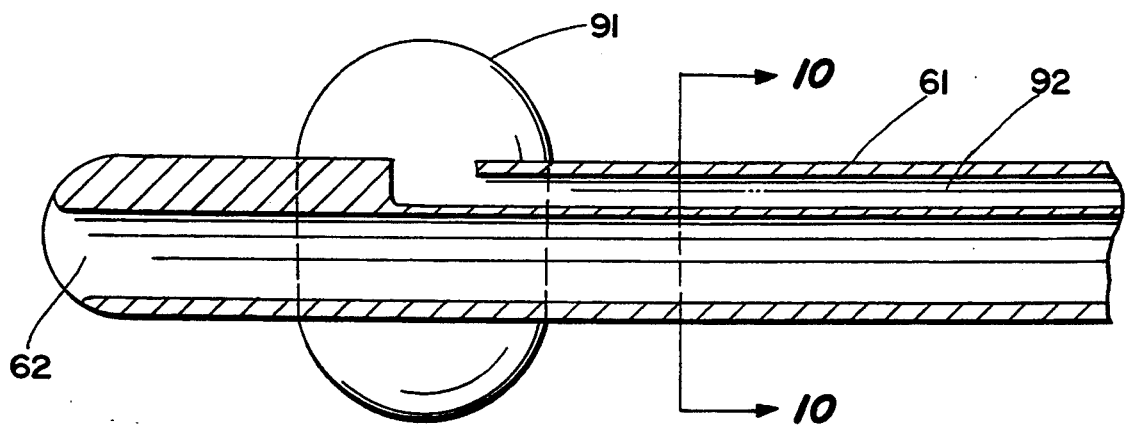
FIG. 9 is a cross-sectional view of the distal tip of an alternate embodiment of the duodenal catheter having an inflatable balloon to facilitate passage into the jejunum or ileum.

It may be desirable to advance the duodenal catheter beyond the duodenum, as for example in the case of intestinal blockage, or for feeding into the jejunum. In such an event, it might be desirable to have a modified duodenal catheter having an inflatable portion on its distal tip. Turning now to FIG. 9, such an alternate embodiment of a duodenal catheter is shown in which the inflatable member 91 is located just proximal to a feeding/aspiration port 62 near the distal tip of the duodenal catheter. The inflation of the balloon 91 with 2-3 ml of a fluid facilitates passage of the tip of the duodenal catheter through the duodenum into the jejunum by means of muscular contractions of the wall of the duodenum. After the tube has reached a desired point, the balloon can be deflated.

Figure 10:
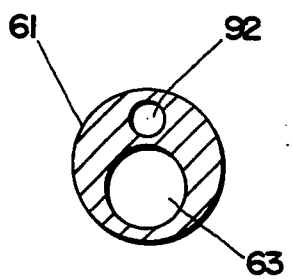
FIG. 10 is a cross-sectional view of the duodenal catheter of FIG. 9 along line 10—10.

A cross-sectional view of the alternate embodiment of the duodenal catheter is shown in FIG. 10. It is characterized by a feeding/aspiration conduit 63 and a balloon inflating lumen 92. The tube itself may be quite small and flexible inasmuch as it is inserted through an introducer tube and it does not have to have the rigidity of the introducer tube in order to get through the esophagus into the stomach. Thus, it is possible to use a duodenal catheter having a very small diameter such as approximately that of a 14 to 18 gauge needle.

Figure 11:
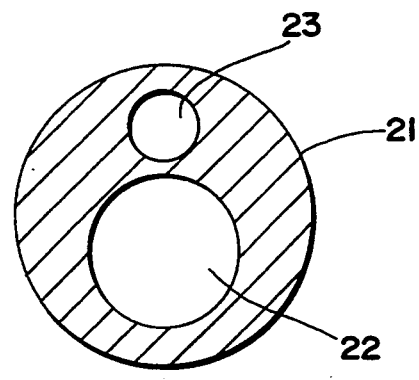
FIG. 11 is a cross-sectional view of the duodenal catheter introducer tube of FIG. 2a along line 11—11.

A cross-sectional view of the introducer tube 20 is shown in FIG. 11. The introducer tube, preferably made of an elastomer such as silicone, polyurethane or latex, is double lumen. Since a variety of catheters of different outer diameters are used for imaging, feeding and aspiration or intestinal blockage, the larger catheter lumen 22 is dimensioned to permit the passage of a variety of duodenal catheters. The inflating lumen 23 may be of any functionally appropriate size.

Figure 12:
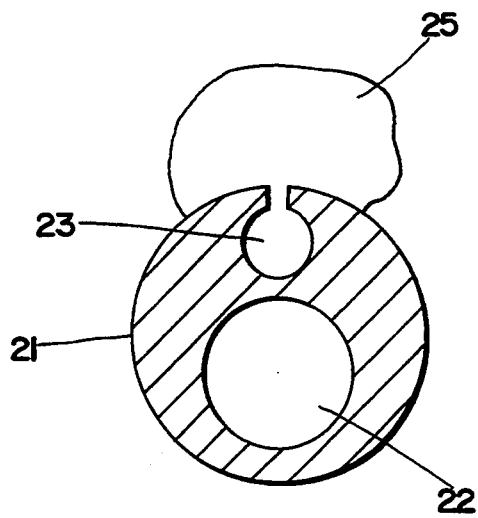
FIG. 12 is a cross-sectional view of the distal tip of the introducer tube of FIG. 2a viewed along line 12—12.
Figure 13:
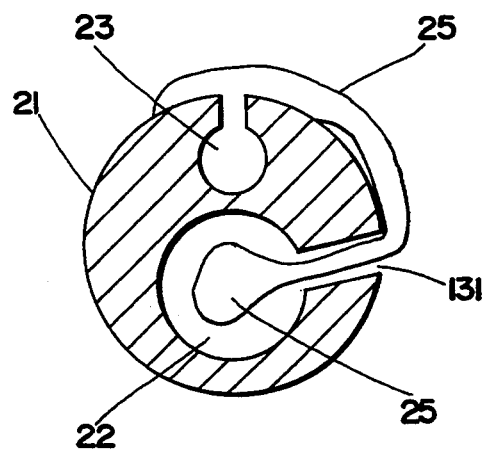
FIG. 13 shows the inflatable balloon of FIG. 12 stuffed into the central conduit of the introducer tube to minimize bulk and to facilitate introduction of the introducer tube through an orifice.

The introducer tube 20 with the anatomically-conforming balloon 25 affixed thereto may be too bulky for insertion into some chambers. In such an event, it may be desirable to house the uninflated, flaccid balloon in a compartment within the introducer tube prior to inflation. FIG. 12 shows a cross-sectional view of the tip of the introducer tube with the flaccid balloon 25 projecting outward from the tube prior to inflation. FIG. 13 shows a possible solution to this problem. The wall 21 of the introducer tube 20 is slit 131 so as to provide an opening into a compartment within the introducer tube. The balloon may be tucked or stuffed into the compartment prior to inserting the introducer tube into the chamber. In FIG. 13, the conduit 22 serves as the compartment prior to inflation. When it is determined that the balloon is within the chamber, inflation of the balloon will cause the balloon to expand and pull out of the compartment, expanding into the chamber and conforming with the interior shape of the chamber. Once the balloon is inflated, the lumen or conduit 22 is clear for insertion of a duodenal catheter.

When the duodenal catheter introducer tube 20 is introduced into the stomach, it may be desirable to aspirate the gastric contents prior to inflation of the anatomically conforming balloon. This prevents reflux of displaced gastric contents during inflation and reduces the incidence of aspiration pneumonia subsequent to the placement of the duodenal catheter.

It is observed that the catheter introducer tube of the present invention is particularly useful for passing a catheter through non-aligned openings or fenestrations in the wall of an asymmetric chamber such as the stomach. The term "asymmetric chamber", as used herein, means a chamber which has a rotational axis consisting of a straight line drawn between two openings in the wall of the chamber in which the rotational axis does not have a rotational symmetry greater than two-fold. That is, any rotation of the chamber about such a rotational axis will not leave the chamber in a position which is indistinguishable from its position prior to rotation for any angle other than 180°. For example, a cylindrical chamber (having opposed openings on either end) such as a segment of a blood vessel has a rotational axis of infinite symmetry. That is, rotation of the (cylindrical) chamber through any angle, no matter how small or large, about the axis of rotation leaves the chamber spatially indistinguish-able from its position for any other rotation. A stomach has a single-fold rotational axis of symmetry. Only a 360° rotation about the rotational axis (a line connecting the esophageal orifice and the pylorus) will leave the chamber indistinguishable from its position prior to rotation. It follows that the anatomically conforming inflatable balloon must, when inflated, have a shape either similar to or congruous to the shape of an asymmetric chamber. Thus, the term "asymmetric balloon" as used hereinafter, refers to an inflatable balloon which has an inflated shape either similar or congruous to the shape of an asymmetric chamber.

The foregoing description of the preferred embodiment of the invention has been presented for purposes of illustration and description. It is not intended to be exhaustive or to limit the invention to the precise form disclosed. Obvious modifications or variations are possible in light of the above teachings. The embodiment was chosen and described to provide the best illustration of the principles of the invention and its practical application to thereby enable one of ordinary skill in the art to utilize the invention in various embodiments and with various modifications as are suited to the particular use contemplated. It is clear that the use of an inflatable anatomically-conforming balloon to direct a lumen or conduit which enables the passage of a catheter through a chamber can be applied to chambers other than the stomach such as the bladder, uterus, sinuses or any chamber having two or more openings thereinto. All such modifications and variations are within the scope of the invention as determined by the appended claims when interpreted in accordance with the breadth to which they are fairly, legally and equitably entitled.

What I claim is:

1. A catheter introducer tube for insertion into a portaled stomach chamber, thereafter providing an interior conduit between first and second openings in the wall of the stomach chamber, the interior of the stomach chamber having an anatomical shape, said catheter introducer tube comprising a flexible elongate tubular member having: (a) a proximal end and a distal end and first and second lumens therebetween, said first lumen being said internal conduit and said first lumen being dimensioned to permit the passage of a catheter therethrough; (b) an outer wall coextensive with said elongate tubular member; (c) an inflatable balloon anatomically conforming to the stomach affixed to said outer wall substantially adjacent to the distal end thereof, the interior of said anatomically conforming balloon being in fluid communication with said second lumen and wherein said distal tip of the introducer tube is substantially adjacent to the second opening in the stomach chamber wall following inflation of the anatomically conforming balloon within said stomach chamber.

2. The catheter introducer tube of claim 1 wherein the catheter introducer tube further comprises a mark near the proximal end thereof, said mark providing a visual index of the rotational orientation of said balloon within the stomach.

3. The catheter introducer tube of claim 2 further comprising an externally detectable marker proximal and adjacent to said anatomically conforming balloon.

* * * * *

UNITED STATES PATENT AND TRADEMARK OFFICE
CERTIFICATE OF CORRECTION

PATENT NO. : 5,401,241
DATED : March 28, 1995
INVENTOR(S) : Harry M. Delany

It is certified that error appears in the above-indentified patent and that said Letters Patent is hereby corrected as shown below:

On the title page: Item [73] Assignee should read:

-- Albert Einstein College of Medicine of Yeshiva University, 1300 Morris Park Avenue, Bronx, New York 10461 --

Signed and Sealed this

Fifteenth Day of October, 1996

Attest:

BRUCE LEHMAN

Attesting Officer  Commissioner of Patents and Trademarks